(12) United States Patent
Gunn

(10) Patent No.: US 9,572,712 B2
(45) Date of Patent: Feb. 21, 2017

(54) OSMOTICALLY ACTUATED FLUIDIC VALVE

(71) Applicant: Novartis AG, Basel (CH)

(72) Inventor: Nicholas Max Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 176 days.

(21) Appl. No.: 14/090,192

(22) Filed: Nov. 26, 2013

(65) Prior Publication Data

US 2014/0172090 A1 Jun. 19, 2014

Related U.S. Application Data

(60) Provisional application No. 61/737,959, filed on Dec. 17, 2012.

(51) Int. Cl.
| | | |
|---|---|---|
| *A61M 5/00* | (2006.01) | |
| *A61F 9/007* | (2006.01) | |
| *A61N 1/04* | (2006.01) | |
| *A61N 1/05* | (2006.01) | |

(52) U.S. Cl.
CPC ........ *A61F 9/00781* (2013.01); *A61N 1/0428* (2013.01); *A61N 1/0543* (2013.01)

(58) Field of Classification Search
CPC .................. A61M 5/14276; A61F 9/00781
See application file for complete search history.

(56) References Cited

U.S. PATENT DOCUMENTS

| | | | |
|---|---|---|---|
| 4,089,329 | A | 5/1978 | Couvillon, Jr. et al. |
| 4,206,762 | A | 6/1980 | Cosman |
| 4,457,757 | A | 7/1984 | Molteno |
| 4,560,375 | A | 12/1985 | Schulte et al. |

(Continued)

FOREIGN PATENT DOCUMENTS

| | | |
|---|---|---|
| CN | 101360523 | 2/2009 |
| CN | 101466299 | 6/2009 |

(Continued)

OTHER PUBLICATIONS

International Searching Authority, International Search Report, PCT/US2012/66709, Apr. 19, 2013, 4 pages.

(Continued)

*Primary Examiner* — Leslie Deak

(57) ABSTRACT

An implantable fluidic valve actuated by osmotic pressure gradient and methods of operating it are provided. The valve includes: an input fluid channel; an output fluid channel in fluid communication with the input fluid channel at an aperture; and a semi-permeable membrane forming a portion of a sealed chamber. The semi-permeable membrane may have an outer surface forming a wall of the input fluid channel, and an inner surface forming a wall of the sealed chamber, the membrane being configured to allow diffusion of a solvent into and out of the sealed chamber; and a first electrode and a second electrode disposed within the sealed chamber configured to receive a voltage. A pump including the above elements and a check valve is provided. An ocular implant including an inlet tube sized to receive aqueous humor and an intra-ocular pressure control system having a fluidic valve as above is also provided.

20 Claims, 8 Drawing Sheets

(56) References Cited

U.S. PATENT DOCUMENTS

| | | |
|---|---|---|
| 4,604,087 A | 8/1986 | Joseph |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters, Jr. et al. |
| 5,005,577 A | 4/1991 | Frenkel |
| 5,083,742 A | 1/1992 | Wylie et al. |
| 5,171,132 A | 12/1992 | Miyazaki et al. |
| 5,178,604 A | 1/1993 | Baerveldt et al. |
| 5,179,953 A | 1/1993 | Kursar |
| 5,397,300 A | 3/1995 | Baerveldt et al. |
| 5,433,701 A | 7/1995 | Rubinstein |
| 5,466,233 A | 11/1995 | Weiner et al. |
| 5,476,445 A | 12/1995 | Baerveldt et al. |
| 5,558,629 A | 9/1996 | Baerveldt et al. |
| 5,573,646 A | 11/1996 | Saito et al. |
| 5,626,558 A | 5/1997 | Suson |
| 5,681,275 A | 10/1997 | Ahmed |
| 5,702,618 A | 12/1997 | Saaski et al. |
| 5,707,643 A | 1/1998 | Ogura et al. |
| 5,722,948 A | 3/1998 | Gross |
| 5,891,097 A | 4/1999 | Saito et al. |
| 5,910,110 A | 6/1999 | Bastable |
| 6,007,511 A | 12/1999 | Prywes |
| 6,048,328 A * | 4/2000 | Haller ............... A61M 5/14276 604/131 |
| 6,050,970 A | 4/2000 | Baerveldt |
| 6,056,269 A | 5/2000 | Johnson et al. |
| 6,240,962 B1 | 6/2001 | Tai et al. |
| 6,251,090 B1 | 6/2001 | Avery et al. |
| 6,261,256 B1 | 7/2001 | Ahmed |
| 6,443,893 B1 | 9/2002 | Schnakenberg et al. |
| 6,447,449 B1 | 9/2002 | Fleischman et al. |
| 6,468,283 B1 | 10/2002 | Richter et al. |
| 6,533,733 B1 | 3/2003 | Ericson et al. |
| 6,579,235 B1 | 6/2003 | Abita et al. |
| 6,589,198 B1 | 7/2003 | Soltanpour et al. |
| 6,682,500 B2 * | 1/2004 | Soltanpour ......... A61F 9/00781 604/521 |
| 6,712,764 B2 | 3/2004 | Jeffries et al. |
| 6,719,750 B2 | 4/2004 | Varner et al. |
| 6,726,676 B2 | 4/2004 | Stegmann et al. |
| 6,749,568 B2 | 6/2004 | Fleischman et al. |
| 6,939,299 B1 | 9/2005 | Petersen et al. |
| 6,962,573 B1 | 11/2005 | Wilcox |
| 6,976,982 B2 | 12/2005 | Santini, Jr. et al. |
| 7,025,740 B2 | 4/2006 | Ahmed |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,304,334 B2 | 12/2007 | Agarwal et al. |
| 7,354,416 B2 | 4/2008 | Quiroz-Mercado et al. |
| 7,409,863 B2 | 8/2008 | Bateman et al. |
| 7,544,176 B2 | 6/2009 | Rodgers et al. |
| 7,612,328 B2 | 11/2009 | Kaiser |
| 7,648,465 B2 | 1/2010 | Gordon |
| 7,756,559 B2 | 7/2010 | Abreu |
| 7,824,699 B2 | 11/2010 | Ralph et al. |
| 8,123,687 B2 | 2/2012 | Dacquay et al. |
| 8,182,435 B2 | 5/2012 | Dacquay et al. |
| 8,206,440 B2 | 6/2012 | Guarnieri |
| 8,257,295 B2 | 9/2012 | Rickard et al. |
| 8,419,673 B2 | 4/2013 | Rickard |
| 8,545,431 B2 | 10/2013 | Rickard |
| 8,549,925 B2 | 10/2013 | Tai et al. |
| 8,579,848 B2 | 11/2013 | Field et al. |
| 8,585,631 B2 | 11/2013 | Dacquay |
| 8,585,664 B2 | 11/2013 | Dos Santos et al. |
| 8,603,024 B2 | 12/2013 | Bohm et al. |
| 8,652,085 B2 | 2/2014 | Gelvin et al. |
| 8,721,580 B2 | 5/2014 | Rickard et al. |
| 8,753,305 B2 | 6/2014 | Field et al. |
| 8,814,820 B2 | 8/2014 | Bergheim et al. |
| 8,840,578 B2 | 9/2014 | Dos Santos et al. |
| 8,858,491 B2 | 10/2014 | Field et al. |
| 8,864,701 B2 | 10/2014 | Dos Santos et al. |
| 8,986,240 B2 | 3/2015 | Dos Santos et al. |
| 9,072,588 B2 | 7/2015 | Bohm et al. |
| 9,125,721 B2 | 9/2015 | Field |
| 9,132,034 B2 | 9/2015 | Dos Santos |
| 2001/0000527 A1 | 4/2001 | Yaron et al. |
| 2002/0013545 A1 | 1/2002 | Soltanpour et al. |
| 2002/0013546 A1 | 1/2002 | Grieshaber et al. |
| 2002/0019607 A1 | 2/2002 | Bui |
| 2002/0049374 A1 | 4/2002 | Abreu |
| 2002/0087111 A1 * | 7/2002 | Ethier ................ A61F 9/00781 604/9 |
| 2002/0099359 A1 | 7/2002 | Santini, Jr. et al. |
| 2002/0103412 A1 | 8/2002 | Trimmer |
| 2002/0139947 A1 | 10/2002 | Wang |
| 2002/0143284 A1 | 10/2002 | Tu et al. |
| 2002/0156413 A1 | 10/2002 | Williams et al. |
| 2002/0156461 A1 | 10/2002 | Joshi |
| 2002/0165478 A1 | 11/2002 | Gharib et al. |
| 2002/0169468 A1 | 11/2002 | Brown |
| 2002/0175191 A1 | 11/2002 | Joshi et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0146401 A1 | 8/2003 | Wetzel et al. |
| 2003/0225318 A1 | 12/2003 | Montegrande et al. |
| 2003/0234376 A1 | 12/2003 | Cabuz et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0073156 A1 | 4/2004 | Brown |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0228734 A1 | 11/2004 | Jeon et al. |
| 2004/0254438 A1 | 12/2004 | Chuck et al. |
| 2004/0254517 A1 | 12/2004 | Quiroz-Mercado et al. |
| 2005/0016866 A1 | 1/2005 | Kramer et al. |
| 2005/0049578 A1 | 3/2005 | Tu et al. |
| 2005/0067029 A1 | 3/2005 | Henning et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0041220 A1 | 2/2006 | Boukhny et al. |
| 2006/0131350 A1 | 6/2006 | Schechter et al. |
| 2006/0189916 A1 | 8/2006 | Bas |
| 2007/0019156 A1 | 1/2007 | Fink |
| 2007/0032757 A1 | 2/2007 | Medow et al. |
| 2007/0077270 A1 | 4/2007 | Wen |
| 2007/0106199 A1 | 5/2007 | Krivoy et al. |
| 2007/0106200 A1 | 5/2007 | Levy |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0156079 A1 | 7/2007 | Brown |
| 2007/0212397 A1 | 9/2007 | Roth |
| 2007/0243111 A1 | 10/2007 | Momose |
| 2007/0251592 A1 | 11/2007 | Christenson et al. |
| 2007/0255262 A1 | 11/2007 | Haase |
| 2008/0015421 A1 | 1/2008 | Penner |
| 2008/0027478 A1 | 1/2008 | Connors et al. |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2008/0257915 A1 | 10/2008 | Wold |
| 2009/0069648 A1 | 3/2009 | Irazoqui et al. |
| 2009/0076367 A1 | 3/2009 | Sit et al. |
| 2009/0143713 A1 | 6/2009 | Van Dam et al. |
| 2009/0196903 A1 | 8/2009 | Kliman |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0114006 A1 | 5/2010 | Baerveldt |

(56) References Cited

U.S. PATENT DOCUMENTS

| | | |
|---|---|---|
| 2010/0121248 A1 | 5/2010 | Yu et al. |
| 2010/0121348 A1 | 5/2010 | van der Burg et al. |
| 2010/0122733 A1 | 5/2010 | Grygus et al. |
| 2010/0174272 A1 | 7/2010 | Weiner |
| 2010/0222769 A1 | 9/2010 | Meng et al. |
| 2010/0222770 A1 | 9/2010 | Gordon et al. |
| 2010/0234717 A1 | 9/2010 | Wismer |
| 2010/0249691 A1 | 9/2010 | Van Der Mooren et al. |
| 2010/0253167 A1 | 10/2010 | Charnley et al. |
| 2010/0280349 A1 | 11/2010 | Dacquay et al. |
| 2010/0305550 A1 | 12/2010 | Meng et al. |
| 2011/0007454 A1 | 1/2011 | Tang |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0077626 A1 | 3/2011 | Baerveldt et al. |
| 2011/0082385 A1 | 4/2011 | Diaz et al. |
| 2011/0144617 A1 | 6/2011 | Meng et al. |
| 2011/0203700 A1 | 8/2011 | Scholten et al. |
| 2011/0248671 A1 | 10/2011 | Dos Santos et al. |
| 2011/0282328 A1 | 11/2011 | Ambati et al. |
| 2012/0004528 A1 | 1/2012 | Li et al. |
| 2012/0022505 A1 | 1/2012 | Dacquay et al. |
| 2012/0022506 A1 | 1/2012 | Rickard et al. |
| 2012/0039770 A1 | 2/2012 | Namkoong et al. |
| 2012/0296258 A1 | 11/2012 | Rickard et al. |
| 2012/0302861 A1 | 11/2012 | Marshall et al. |
| 2012/0316492 A1 | 12/2012 | Chappel |
| 2013/0000765 A1 | 1/2013 | Fernandes et al. |
| 2013/0085440 A1* | 4/2013 | Bohm .................. A61F 9/00781 604/9 |
| 2013/0144202 A1 | 6/2013 | Field et al. |
| 2013/0150774 A1 | 6/2013 | Field et al. |
| 2013/0150775 A1 | 6/2013 | Dos Santos et al. |
| 2013/0150777 A1 | 6/2013 | Bohm et al. |
| 2013/0150778 A1 | 6/2013 | Dos Santos |
| 2013/0150779 A1 | 6/2013 | Field |
| 2013/0158381 A1 | 6/2013 | Rickard |
| 2013/0204177 A1 | 8/2013 | Field et al. |
| 2013/0211311 A1 | 8/2013 | Field |
| 2013/0211312 A1 | 8/2013 | Gelvin |
| 2013/0218064 A1 | 8/2013 | Rickard |
| 2013/0317413 A1 | 11/2013 | Field et al. |
| 2013/0338564 A1 | 12/2013 | Rickard et al. |
| 2014/0039374 A1 | 2/2014 | Dos Santos et al. |
| 2014/0107557 A1 | 4/2014 | Dos Santos et al. |
| 2014/0163448 A1 | 6/2014 | Lind et al. |
| 2014/0166140 A1 | 6/2014 | Santos et al. |
| 2014/0171777 A1 | 6/2014 | Sanchez et al. |
| 2014/0172090 A1 | 6/2014 | Gunn |
| 2015/0057523 A1 | 2/2015 | Gunn |
| 2015/0057592 A1 | 2/2015 | Gunn |
| 2015/0057593 A1 | 2/2015 | Johnson et al. |
| 2015/0057595 A1 | 2/2015 | Gunn et al. |
| 2015/0057596 A1 | 2/2015 | Lind et al. |
| 2015/0150720 A1 | 6/2015 | Gunn et al. |
| 2015/0230982 A1 | 8/2015 | Gunn et al. |
| 2015/0230984 A1 | 8/2015 | Gunn |

FOREIGN PATENT DOCUMENTS

| | | |
|---|---|---|
| DE | 4438201 | 5/1996 |
| EP | 0102747 | 3/1984 |
| EP | 1195523 | 4/2002 |
| EP | 1296067 | 3/2003 |
| EP | 1917987 | 5/2008 |
| JP | 03049775 | 8/1992 |
| JP | 2005535392 | 11/2005 |
| JP | 2007512866 | 5/2007 |
| WO | WO9303665 | 3/1993 |
| WO | WO9803665 | 1/1998 |
| WO | WO9803809 | 1/1998 |
| WO | WO9938470 | 8/1999 |
| WO | WO0174427 | 10/2001 |
| WO | WO0194784 | 12/2001 |
| WO | WO02056758 | 7/2002 |
| WO | WO03001991 | 1/2003 |
| WO | WO03102632 | 12/2003 |
| WO | WO2004014218 | 2/2004 |
| WO | WO2005079204 | 9/2005 |
| WO | WO2005088417 | 9/2005 |
| WO | WO2007127305 | 11/2007 |
| WO | WO2007136993 | 11/2007 |
| WO | WO2008060649 | 5/2008 |
| WO | WO2008061043 | 5/2008 |
| WO | WO2008084350 | 7/2008 |
| WO | WO2008094672 | 8/2008 |
| WO | WO2009010799 | 1/2009 |
| WO | WO2009026499 | 2/2009 |
| WO | WO2009049686 | 4/2009 |
| WO | WO2009081031 | 7/2009 |
| WO | WO2010129446 | 11/2010 |
| WO | WO2010136071 | 12/2010 |
| WO | WO2011034727 | 3/2011 |
| WO | WO2011034738 | 3/2011 |
| WO | WO2011034740 | 3/2011 |
| WO | WO2011034742 | 3/2011 |
| WO | WO2011035218 | 3/2011 |
| WO | WO2012012017 | 1/2012 |
| WO | WO2013052332 | 4/2013 |
| WO | WO2013058943 | 4/2013 |
| WO | WO2013085894 | 6/2013 |
| WO | WO2013085895 | 6/2013 |
| WO | WO2013090006 | 6/2013 |
| WO | WO2013090231 | 6/2013 |
| WO | WO2013123142 | 8/2013 |

OTHER PUBLICATIONS

International Searching Authority, Written Opinion of the International Searching Authority, PCT/US2012/66709, Apr. 19, 2013, 5 pages.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, International Search Report, PCT/US2010/033329, Jul. 13, 2010, 4 pages.

International Searching Authority, Search Report and Written Opinion of the International Searching Authority, PCT/US2010/033329, Jul. 13, 2010, 8 pages.

International Searching Authority, International Search Report, PCT/US2010/047429, Nov. 1, 2010, 4 pages.

International Searching Authority, Written Opinion of the International Searching Authority, PCT/US2010/047429, Nov. 1, 2010, 7 pages.

International Searching Authority, International Search Report, PCT/US2010/047600, Dec. 14, 2010, 5 pages.

International Searching Authority, Written Opinion of the International Searching Authority, PCT/US2010/047600, Dec. 14, 2010, 7 pages.

International Searching Authority, International Search Report, PCT/US2010/049424, Nov. 26, 2010, 6 pages.

(56) References Cited

OTHER PUBLICATIONS

International Searching Authority, Written Opinion of the International Searching Authority, PCT/US2010/049424, Nov. 26, 2010, 8 pages.
International Searching Authority, International Search Report, PCT/US2011/036742, Aug. 17, 2011, 2 pages.
International Searching Authority, Written Opinion of the International Searching Authority, PCT/US2011/036742, Aug. 17, 2011, 5 pages.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al. "Continuous Measurement of Intraocular Pressure in Rabbits by Telemetry," Investigative Ophthalmology & Visual Science (IVOS), May 1996, pp. 966-975, vol. 37, No. 6, IVOS.
Puers, Robert, "Linking Sensors with Telemetry. Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al. "Initial Investigations on Systems for Measuring Intraocular Pressure," Sensors and Actuators, 2000, p. 287-291, vol. 85, Elsevier Science B.V., Germany.
Stangel, Karsten, et al. "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al. "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al. "An Implantable Telemetric Tonometer for Direct Intraocular Pressure Measurements," 1st European Conference on Biomedical Engineering, Feb. 1991, pp. 194-195, vol. 17, No. 20, Nice, France.
Walter, Peter; Intraocular Pressure Sensor: Where Are We—Where Will We Go? Journal Graefe's Archive for Clinical and Experimental Ophthalmology, Publisher Springer Berline/Heidelberg: ISSN 0721-832X (Print) 1435-702X (Online): Issue vol. 240, No. 5/May 2002 DOI 10.1007/s00417-002-0474-y: pp. 335-336; Subject Collection Medicine.
Neagu Cristina R.; "A Medical Microactuator Based on an Electrochemical Principle"; Thesis at the Twente University,the Netherlands, Enschede; Aug. 28, 1998; pp. 1-162.
Saloomeh Saati M.D., et al.; "Mini Drug Pump for Ophthalmic Use"; Trans Am Ophthalmol Soc 2009; 107; pp. 60-71.
Stemme et al.; "A Valveless Diffuser/Nozzle-Based Fluid Pump"; ScienceDirect; Sensors and Actuators A, 39; pp. 159-167 (1993).
Nisar, et al.; MEMS-Based Micropumps in Drug Delivery and Biomedical Applications; ScienceDirect; Sensors and Actuators B 130; pp. 917-942 (2008).
International Searching Authority, International Search Report, PCT US2010/047605; Dec. 16, 2010, 7 pages.
International Searching Authority, Written Opinion of the International Searching Authority, PCT US2010/047605; Dec. 16, 2010, 9 pages.
International Searching Authority, International Search Report, PCT/US2010/047612; Dec. 21, 2010, 7 pages.
International Searching Authority, Written Opinion of the International Searching Authority, PCT/US2010/047612; Dec. 21, 2010, 10 pages.

Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press. New York", pp. 7-43.
Yasukawa T et al., 2001, "Biodegradable scleral plugs for vitreoretinal drug delivery", Adv. Drug Del Rev., 52(1), 25-36.
International Searching Authority, International Search Report PCT/US2013/026066, Apr. 17, 2013. 5 pages.
International Searching Authority, Written Opinion of the International Searching Authority, PCT/US2013/026066, Apr. 17, 2013, 8 pages.
Parkhutik, Vitali, et al., The Role of Hydrogen in the Formation of Porous Structures in Silicon, Materials Science & Engineering, 1999, B58, 95-99, Elsevier Science, S.A.
Dacquay, Bruno, Intraocular Pressure Sensor, Prosecution History, U.S. Appl. No. 12/434,709, filed May 4, 2009, 566 pages.
Rickard, Matthew J.A., Lumen Clearing Valve for Glaucoma Drainage Device, Prosecution History, U.S. Appl. No. 12/609,043, filed Oct. 30, 2009, 1507 pages.
Rickard, Matthew, Intraocular Pressure Sensor with External Pressure Compensation, Prosecution History, U.S. Appl. No. 12/563,244, filed Sep. 21, 2009, 562 pages.
Dos Santos, Cesario, Power Generator for Glaucoma Drainage Device, Prosecution History, U.S. Appl. No. 12/685,772, filed Jan. 12, 2010, 517 pages.
Dacquay, Bruno, Closed Loop Glaucoma Drug Delivery System, Prosecution History, U.S. Appl. No. 13/109,155, filed May 17, 2011, 238 pages.
Field, Leslie, Active Drainage Systems with Pressure-Driven Valves and Electronically-Driven Pump, Prosecution History, U.S. Appl. No. 13/315,329, filed Dec. 9, 2011, 1620 pages.
Rickard, Matthew J.A., Power Saving Glaucoma Drainage Device, Prosecution History, U.S. Appl. No. 12/837,803, filed Jul. 16, 2010, 1725 pages.
Dos Santos, Cecario P., Multilayer Membrane Actuators, Prosecution History, U.S. Appl. No. 13/315,905, filed Dec. 9, 2011, 1652 pages.
Rickard, Matthew, Intraocular Pressure Sensor with External Pressure Compensation, Prosecution History, U.S. Appl. No. 14/267,443, filed May 1, 2014, 53 pages.
Rickard, Matthew, Intraocular Pressure Sensor with External Pressure Compensation, Prosecution History, U.S. Appl. No. 13/565,907, filed Aug. 3, 2012, 1652 pages.
Barton, Keith, et al., "The Ahmed Baerveldt Comparison Study," Journal of Ophthalmology, Jul. 15, 2010, vol. 118, No. 3, Elsevier, Inc., USA.
International Searching Authority, Search Report of the International Searching Authority, PCT/US2012/057261, Jan. 23, 2013, 7 pages.
International Searching Authority, Written Opinion of the International Searching Authority, PCT/US2012/057261, Jan. 23, 2013, 8 pages.
International Searching Authority, International Search Report, PCT/US2014/039582, Oct. 22, 2014, 3 pages.
International Searching Authority, Written Opinion, PCT/US2014/039582, Oct. 22, 2014, 3 pages.
Mokwa et al., "Mircro-Transponder Systems for Medical Applications", IEEE Transactions on Instrumentation and Measurement, vol. 50, No. 6, Dec. 2001, 5 pgs.
International Searching Authority, Search Report and Written Opinion, PCT/US2013/074113, Apr. 18, 2014, 10 pages.
Driot et al.; "Ocular pharmacokinetics of fluocinolone acetonide after RetisertTM intravitreal implantation in rabbits over a 1-year period"; J. Ocular Pharm; 20; 3; 2004, pp. 269-275.
Glybina et al.; "Neuroprotective properties of fluocinolone acetonide chronically delivered into the vitreous of albino RCS rats"; IVOS; 47; 2006; ARVO e-Abstract 1028.

\* cited by examiner

OSMOTICALLY ACTUATED FLUIDIC VALVE

PRIORITY CLAIM

This application claims the benefit of priority of U.S. Provisional Patent Application Ser. No. 61/737,959 titled "OSMOTICALLY ACTUATED FLUIDIC VALVE," filed on Dec. 17, 2012, whose inventor is Nicholas Max Gunn, which is hereby incorporated by reference in its entirety as though fully and completely set forth herein.

FIELD OF THE INVENTION

Embodiments described herein relate to the field of osmotically actuated fluidic valves. More particularly, embodiments described herein are related to the field of fluidic valves for ocular implants in ophthalmic treatment of diseases such as Glaucoma.

DESCRIPTION OF RELATED ART

Glaucoma, a group of eye diseases affecting the retina and optic nerve, is one of the leading causes of blindness worldwide. Most forms of glaucoma result when the intraocular pressure (IOP) increases above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Also shown in FIG. 1 are posterior chamber 170 and anterior chamber 175. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. Some embodiments of drainage devices include MEMS (Micro Electro-Mechanical Systems) fluidics valves that are low power and only require power to change their state. However, these valves are typically bi-positional: either fully opened or fully closed, and cannot be set at variable positions.

Therefore, there is a need for simple and compact drainage mechanisms to operate active fluidic elements independently for implantable systems.

SUMMARY

According to some embodiments, an implantable fluidic valve actuated by osmotic pressure gradient includes: an input fluid channel; an output fluid channel in fluid communication with the input fluid channel at an aperture; and a semi-permeable membrane forming a portion of a sealed chamber. The semi-permeable membrane may have an outer surface forming a wall of the input fluid channel, and an inner surface forming a wall of the sealed chamber, the membrane being configured to allow diffusion of a solvent into and out of the sealed chamber; and a first electrode and a second electrode disposed within the sealed chamber configured to receive a voltage.

According to some embodiments, an ocular implant for treating an ocular condition includes an inlet tube sized to receive aqueous humor; and an intra-ocular pressure (IOP) control system to regulate drainage of aqueous humor from the inlet tube. In some embodiments, the IOP control system includes a fluidic valve having an input fluid channel coupled to the inlet tube; an output fluid channel in communication with the input fluid channel at an aperture; and a semi-permeable membrane configured to selectively displace relative to the aperture. The membrane may have an outer side adjacent the input fluid channel and an inner side forming a part of a chamber, the chamber including a first electrode and a second electrode configured to affect free ions in the chamber.

In embodiments as disclosed herein, a method for regulating fluid flow in an ocular implant with a valve having a membrane separating an environment fluid from a chamber containing an electrolyte solution may include applying a first current through a first and a second electrode in the chamber; allowing the electrolyte solution to reach osmotic equilibrium with the environment fluid in a manner that modifies the volume of the chamber; applying a second current through the first and the second electrodes in the chamber; allowing the electrolyte solution to reach osmotic equilibrium with the environment fluid in a manner that modifies the volume of the chamber.

In some embodiments, an implantable fluidic pump actuated by osmotic pressure gradient may include an input fluid channel; an output fluid channel in fluid communication with the input fluid channel at an aperture; a semi-permeable membrane forming a portion of a sealed chamber, the semi-permeable membrane having an outer surface forming a wall of the input fluid channel, and having an inner surface forming a wall of the sealed chamber, the membrane being configured to allow diffusion of a solvent into and out of the sealed chamber; a first electrode and a second electrode disposed within the sealed chamber configured to receive a voltage; and an output check valve separating the output fluid channel from an exterior environment.

In some embodiments, an implantable fluidic pump actuated by osmotic pressure gradient may include an input fluid channel; a pump chamber in fluid communication with the input fluid channel; an output fluid channel in fluid communication with the pump chamber; a non-permeable, deformable membrane forming a portion of a sealed chamber, the non-permeable, deformable membrane having an outer surface forming a wall of the pump chamber, and having an inner surface forming a wall of the sealed chamber; a semi-permeable membrane forming a second portion of a sealed chamber and having an outer surface forming a wall of the input fluid and an inner surface forming a wall of the sealed chamber; a first electrode and a second electrode disposed within the sealed chamber configured to receive a voltage; and an output check valve separating the pump chamber from the output fluid channel. The implantable fluidic pump may also include an input check valve separating the pump chamber from the input fluid channel and an outlet check valve separating the pump chamber from the output fluid channel (where the input check valve and the output check valve may be configured to allow an environment fluid to flow from the input channel to the output channel).

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Figure 1:
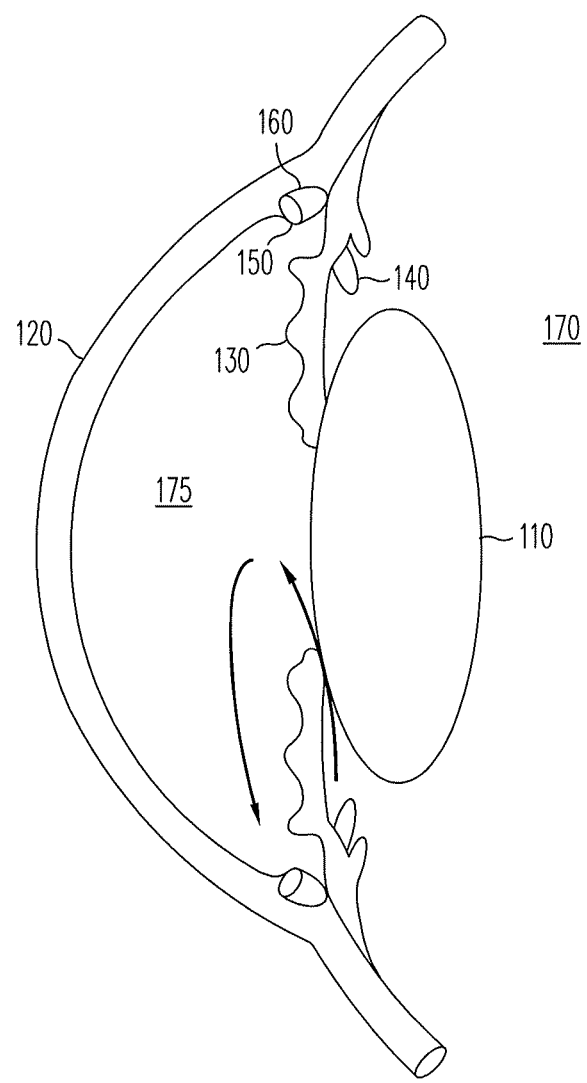
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to a method and system for regulating fluidic flow through an implanted device used to control IOP. In the embodiments disclosed herein, the method and system may utilize osmotic principles to actuate a flow regulator, such as a variable state valve or pump, that increases or decreases drainage flow. Some embodiments operate by changing the number of free ions in a solution within a chamber defined by sealed semi-permeable membrane. Based on the number of free ions, the membrane will inflate or deflate via osmosis, thus opening and closing the flow regulator, such as the variable state valve or pump. The flow regulator is able to control fluidic flow at variable levels while using low amounts of power to maintain valve or pump set points.

Figure 2:
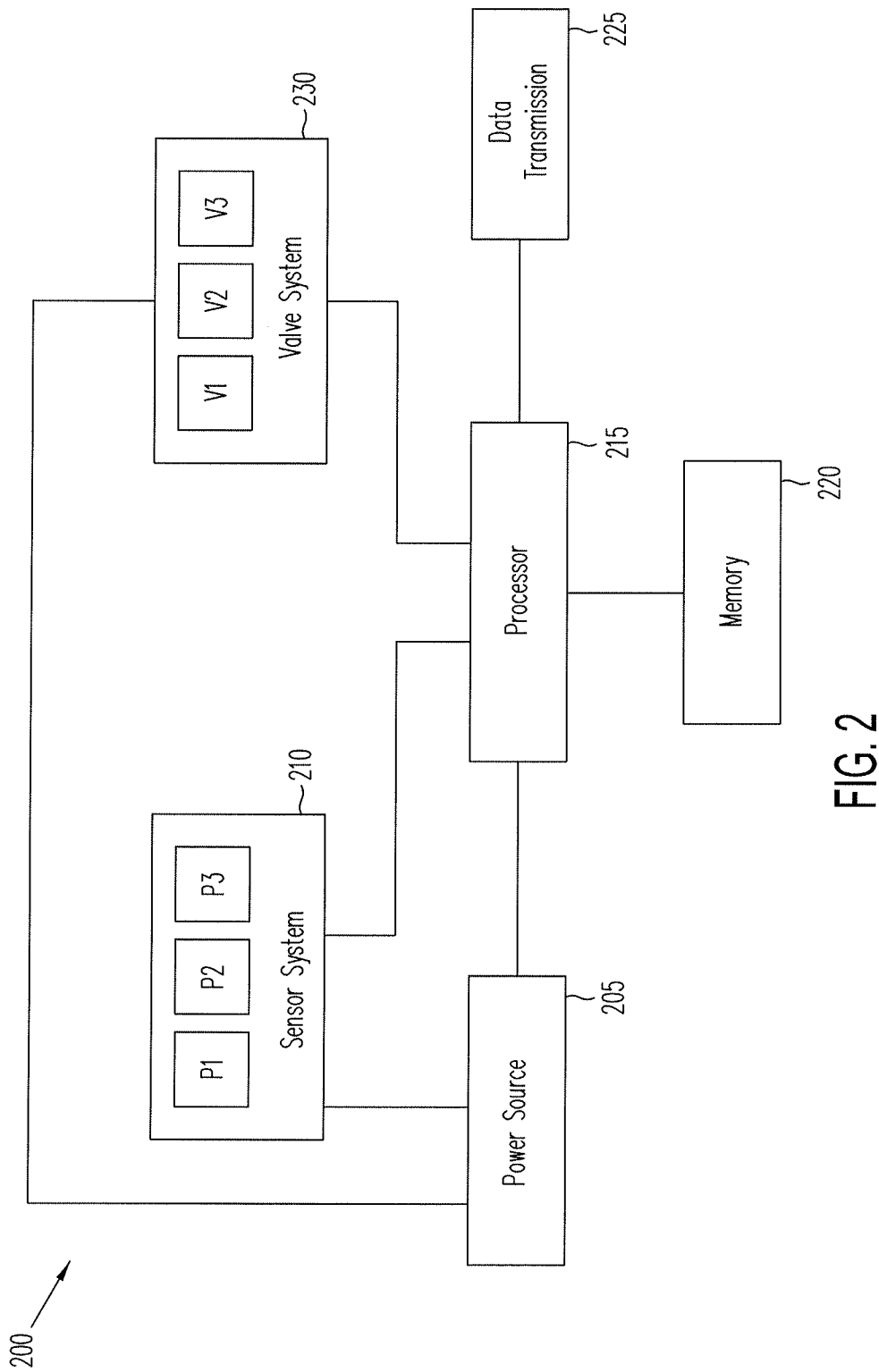
FIG. 2 is a block diagram of an exemplary IOP control system, according to some embodiments.

FIG. 2 is a block diagram of an exemplary IOP control system 200, according to some embodiments. IOP control system 200 may be configured in a manner that provides IOP pressure control, and may also regulate and control bleb pressures, reducing complications arising from surgical implant glaucoma devices. In FIG. 2, IOP control system 200 includes a power source 205, an IOP sensor system 210, a processor 215, a memory 220, a data transmission module 225, and a valve system 230.

In some embodiments processor 215 is an integrated circuit with power, input, and output pins capable of performing logic functions. Processor 215 may be a controller that controls different components performing different functions. Memory 220 may be a semiconductor memory that interfaces with processor 215. It may include executable instructions as performed by processor 215. In one example, processor 215 can write data and commands to, and read data and commands from, memory 220. For example, processor 215 can be configured to read data from sensor system 210 and write that data to memory 220. In this manner, a series of sensed or calculated IOP readings can be stored in memory 220. Processor 215 is also capable of performing other basic memory functions, such as erasing or overwriting memory 220, detecting when memory 220 is full, and other common functions associated with managing semiconductor memory.

Valve system 230 may include a passive valve, a pressure driven valve, an electronically controlled valve, or other type of valve controlling flow of aqueous humor through IOP control system 200. Valve system 230 may include any number of valves and valve types, in combination. Some embodiments also include one or more pumping systems cooperating with one or more valves in valve system 230, providing pressure relief when needed. Pumps are also contemplated and may form a part of the valve system, or a separate part of the IOP control system 200.

As shown in FIG. 2, IOP sensor system 210 includes pressure sensors P1, P2, and P3. These pressure sensors can be any type of pressure sensors suitable for implantation in the eye. Each of pressure sensors P1, P2, and P3 may be the same type of pressure sensor, or they may be different types of pressure sensors.

Generally, IOP is a gauge pressure reading—the difference between the absolute pressure in the eye (e.g. as measured by sensor P1) and atmospheric pressure (e.g. as measured by the sensor P3). For example, in some embodiments sensor P1 may take pressure readings for anterior chamber 175 (as measured by sensor P1), sensor P2 may take pressure readings for a drainage location (as measured by sensor P2) and atmospheric pressure in the vicinity of the eye (as measured by the sensor P3). The pressure readings of sensors P1, P2, and P3 and the results of any calculations can be stored in memory 220 by processor 215. In some embodiments, they can later be read from memory 220 so that actual IOP over time can be interpreted by a physician.

Readings from pressure sensors P1, P2, and P3 can be used to control IOP by adjusting the valve system 230 to stop or throttle flow. Valve system 230 may be controlled by processor 215 based on input data received from sensor system 210. A desired pressure differential (corresponding to a desired flow rate) can be maintained by controlling the operation of the valve system 230. Likewise, various intraocular pressure parameters, such as, by way of non-limiting example, a desired IOP, an IOP change rate, and/or a bleb pressure may be controlled by controlling the operation of valve system 230.

Data transmission module 225 may transmit information from the implanted IOP control system 200 or may receive information, according to some embodiments. In some embodiments, the data transmission module 225 may include a radio-frequency (RF) device using a digital data protocol. It may include one or both of a transmitter and a receiver, and in some embodiments, includes a transceiver. In some embodiments, the data transmission module may communicate with an external unit that may be configured to verify the readings from sensor system 210 indicating the pressure at the dry subconjunctiva under IOP control system 200 or may communicate programming or other information to IOP control system 200.

Figure 3:
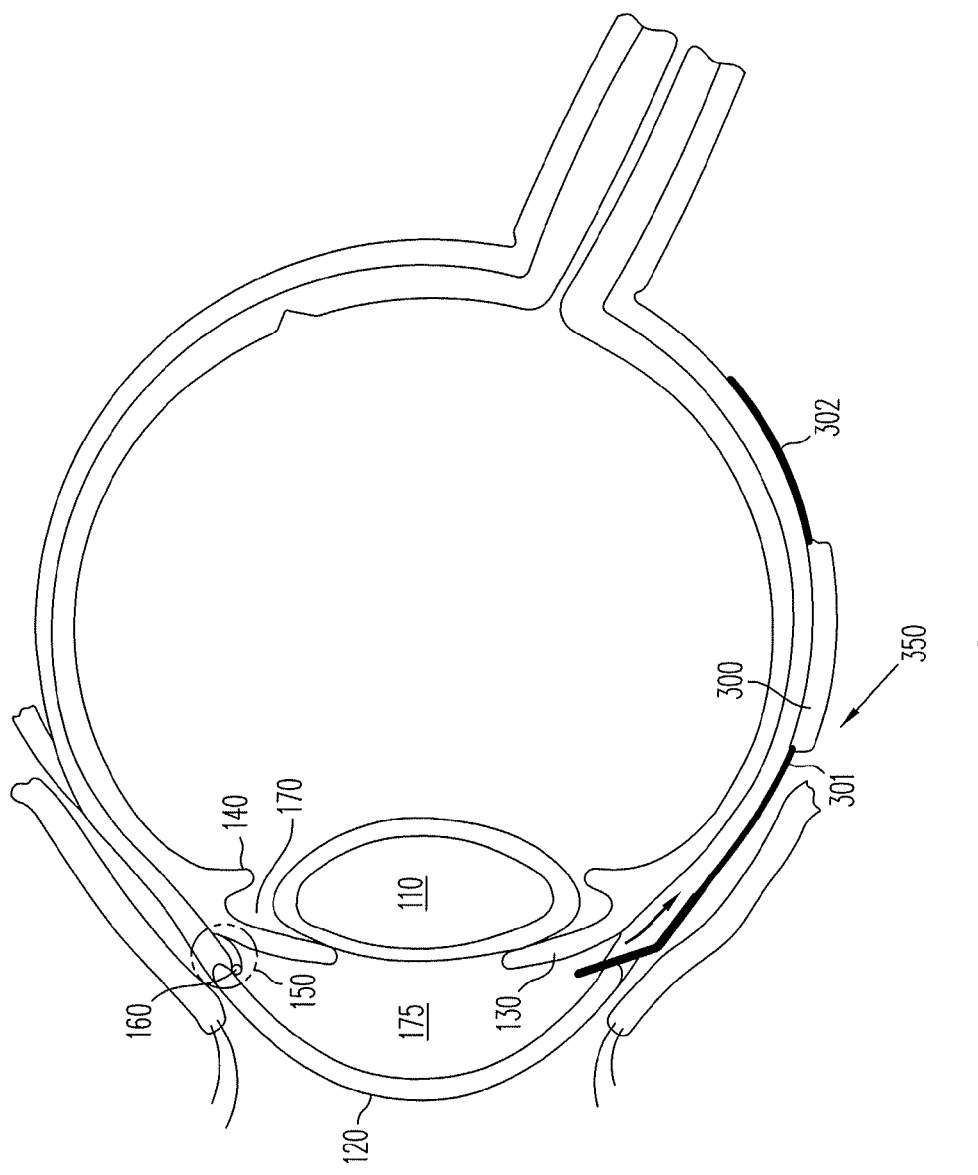
FIG. 3 is a schematic diagram of an ocular implant that carries the IOP control system of FIG. 2, according to some embodiments.

FIG. 3 is a schematic diagram of an ocular implant or drainage device 350 that carries IOP control system 200, according to some embodiments. Drainage device 350 includes a plate 300, an inlet tube 301, and an optional outlet tube 302. Plate 300 is arranged to carry components of IOP control system 200 shown in FIG. 2. For example, plate 300 may include power source 205, elements of sensor system 210, processor 215, memory 220, data transmission module 225, and valve system 230.

Plate 300 is configured to fit at least partially within the subconjunctival space and its dimensions may vary. In some embodiments plate 300 is between about 15 mm×12 mm to about 30 mm×15 mm or an area of approximately 250-350 in$^2$, with a thickness less than about 2 mm, and preferably less than about 1.5 mm. Plate 300 may be formed in a curved shape to the radius of the eye globe (about 0.5 inches). In some embodiments, plate 300 may be rigid and preformed with a curvature suitable to substantially conform to the eye globe or it may be flexible and able to flex to conform to the eye globe. Some embodiments are small enough that conforming to the eye globe provides little benefit in comfort or implantation technique. The above dimensions are exemplary only, and other sizes and arrangements are contemplated herein.

Inlet tube 301 extends from an anterior side of plate 300 and extends into anterior chamber 175. Inlet tube 301 includes an open end and a lumen that extends into an active portion inside plate 300. The active portion inside plate 300 may include IOP control system 200, according to some embodiments. Outlet tube 302 is coupled to the active portion inside plate 300 and includes an open end and a lumen extending to an outer portion of the eye. According to some embodiments, aqueous humor from anterior chamber 175 flows through inlet tube 301 and exits in the vicinity of plate 300, or through outlet tube 302, to a drainage site. In some embodiments, the flow of aqueous humor through drainage device 350 is controlled by the active portion inside plate 300. The drainage site may be in the vicinity of plate 300 or at the open end of outlet tube 302 draining to an alternate location such as the suprachoroidal space or may be proximate to plate 300.

In some embodiments, inlet tube 301 and optional outlet tube 302 drain aqueous humor from the anterior chamber 175 of the eye to the drainage site. Valve system 230 in IOP control system 200, included in plate 300, controls flow of aqueous humor through tubes 301 and 302. In some embodiments, pressure sensor P1 measures pressure at inlet tube 301, upstream from valve system 230 (in plate 300). In this manner, pressure sensor P1 measures pressure in anterior chamber 175.

Optional outlet tube 302 shunts fluid to a drainage location, which may be at any of numerous locations within the eye. In some embodiments, outlet tube 302 may shunt aqueous humor from anterior chamber 175 to the subconjunctival space. Alternatively, outlet tube 302 may shunt aqueous humor from anterior chamber 175 to the subscleral space. In some embodiments, outlet tube 302 may shunt aqueous humor from anterior chamber 175 to the suprachoroidal space, the supraciliary space, the juxta-uveal space, or to the choroid, forming aqueous reservoirs to facilitate absorption in those respective locations. In some embodiments, outlet tube 302 shunts aqueous humor from anterior chamber 175 to Schlemm's canal, a collector channel in Schlemm's canal, or any of a number of different blood vessels like an episcleral vein. In some examples, outlet tube 302 even shunts aqueous humor from anterior chamber 175 to outside the conjunctiva. Each of the different anatomical locations to which aqueous humor is shunted is an example of a drainage location.

Embodiments consistent with the present disclosure include one or more valves such as valves V1, V2, and V3 in valve system 230 (cf. FIG. 2). One or more of these may utilize osmotic principles for actuation. For example, by changing the ion concentration in an electrolyte solution within a sealed semi-permeable membrane, the membrane will inflate or deflate via osmosis, thus opening and closing the valve. The valve is able to control fluidic flow at variable levels while using low amounts of power to maintain valve set points. These valves may be referred to as MEMS-based fluidic devices, and may be used in combination with one or more one-way check valves to make a fluidic pump in some exemplary embodiments.

Figure 4:
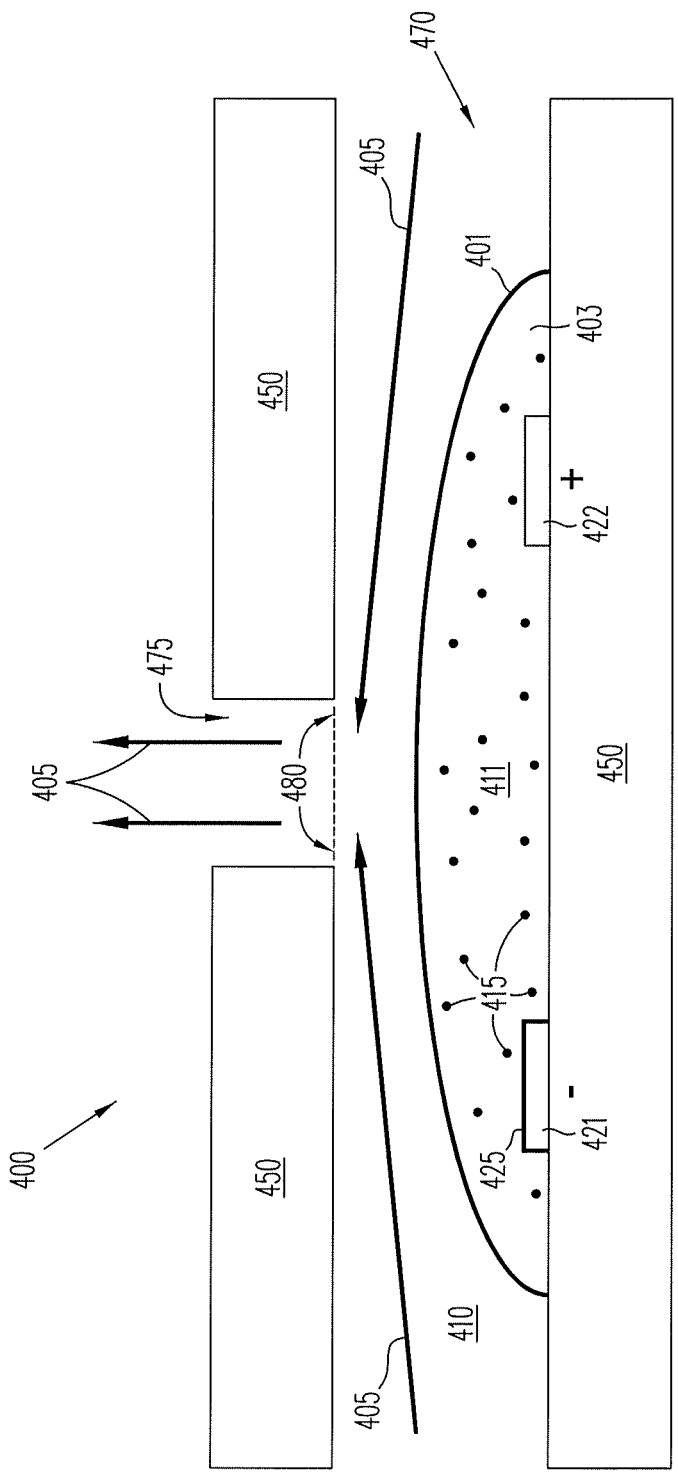
FIG. 4 shows a partial view of an osmotically actuated fluidic valve, according to some embodiments.

FIG. 4 shows a partial view of an osmotically actuated fluidic valve 400 that may form a valve or a part of a valve for a valve system 230, according to some embodiments. Valve 400 includes an input fluidic channel 470 and an output fluidic channel 475 formed into a substrate 450. Input fluidic channel 470 and output fluidic channel 475 communicate through an aperture 480. An environment fluid 410 flows from channel 470 to channel 475 when the valve is fully open, or partially open as illustrated in FIG. 4, as shown by arrows 405. According to some embodiments, input fluidic channel 470 may be coupled to an environment outside of valve 400, such as inlet tube 301 for draining aqueous humor from an eye's anterior chamber 175. In some embodiments, output fluidic channel 475 may be coupled to outlet tube 302, which may lead to a drainage location such as described in detail above (cf. FIG. 3). Thus, according to some embodiments input fluidic channel 470 may be coupled to inlet tube 301, and output fluidic channel 475 may be coupled to outlet tube 302 in ocular implant 350 (cf. FIG. 3).

In the embodiment shown, valve 400 includes a semi-permeable membrane 401 and at least one electrode, referenced by the numerals 421 and 422. Membrane 401 creates a sealed chamber 403 housing the electrodes 421, 422, and encloses a fluid 411 having an electrolyte in solution. Thus, the semi-permeable membrane 401 forms a sealed chamber 403 containing fluid 411. Semi-permeable membrane 401 allows small solvent molecules such as water to diffuse from one side of the membrane to the opposite side of the membrane. Membrane 401 may block the passage of positive or negative ions in an electrolyte solution and non-ionic species in solution from one side of the membrane to the opposite side of the membrane. In some embodiments, membrane 401 is deformable or flexible, so that it expands or contracts with the diffusion of solvent in and out of the membrane, changing the volume of sealed chamber 403. In some embodiments, membrane 401 may include a portion which is semi-permeable and a portion which is deformable or flexible, such as a diaphragm. Further according to some embodiments, sealed chamber 403 may have a semi-permeable membrane portion separated from a deformable or flexible diaphragm.

According to some embodiments, membrane 401 or the diaphragm may flex or deform to block or partially block the aperture 480 fluidly connecting channel 470 to channel 475, thereby reducing or increasing a fluid flow from input fluidic channel 470 to output fluidic channel 475. According to some embodiments, semi-permeable membrane 401, or the semi-permeable portion of membrane 401 may have a thickness between about 2 to 10 microns (1 micron, 1 $\mu m = 10^{-3}$ mm $= 10^{-6}$ m). In some embodiments, the thickness of a semi-permeable membrane included in membrane 401 may be as low as 500 Å (angstroms or $10^{-10}$ meters). In some embodiments, membrane 401 may have a circular shape with a diameter of approximately 500 μm to a few millimeters. The materials used to fabricate a membrane with semi-permeable properties as disclosed herein may be polymers. An example of a polymer that may be used for semi-permeable membrane 401 includes a non-porous material such as Parylene, including Parylene-C, Parylene-N, Parylene-D, and Parylene-HT. Other examples include Polyimide, Poly(methyl methacrylate) (PMMA), or other plastics or epoxies. In some embodiments, a silicone-based material such as Polydimethylsiloxane (PDMS) may be used to form membrane 401. In some embodiments the membrane may comprise a composite of layers such as gold and parylene. Other materials may be used as would be apparent to one of ordinary skill in the art.

As illustrated in FIG. 4, an exterior surface of membrane 401 is in contact with fluid 410. In some embodiments, fluid 410 is an environment fluid having a non-zero osmolarity. For example, in some embodiments fluid 410 may be aqueous humor from anterior chamber 175 in the eye (cf. FIG. 1). Aqueous humor contains salts and ions, such as $Na^+$, $Ca^{++}$, $K^+$, $Cl^-$, and others as well as non-ionic species such as proteins. Thus, aqueous humor typically has non-zero osmolarity. In some embodiments, fluid 410 is collected from the environment in which the valve acts, such as the eye's anterior chamber 175. Electrode 422 and electrode 421 are placed on substrate 450 within chamber 403 enclosed by membrane 401, in electrical contact with fluid 411 inside chamber 403. Electrodes 421 and 422 may have external connections to the power source 205.

The ions dissolved in fluid 411 separate into positive ions 415 and negative ions when a voltage difference is applied between electrodes 422 and 421. Positive ions 415 are displaced towards the proximity of (negatively biased) electrode 421, and in the case of metallic ions some of the ions forming a plating layer 425 on the surface of electrode 421. Thus, fluid 411 changes its osmolarity as positive ions 415 accumulate on the surface of electrode 421, and come out of solution. In some embodiments, the osmolarity of fluid 411 may drop below the osmolarity of environment fluid 410 when plating layer 425 is formed. In such embodiments, equilibrium between the osmolarity of fluid 410 and osmolarity of fluid 411 may be reached through diffusion of a solvent across semi-permeable membrane 401. The solvent may be water molecules diffusing from fluid 410 to fluid 411 through semi-permeable membrane 401. As molecules diffuse through the semi-permeable membrane 401, the volume of the chamber 403 increases, expanding the chamber, and reducing the size of the channel 470. So doing also reduces flow through aperture 480, thereby modifying the drainage rate through the valve.

The osmolarity in fluid 411 is determined by concentration of ions and other dissolved species in solution. As indicated above, the ions in solution in fluid 411 include positive and negative ions. The positive ion concentration is proportional to the number of positive ions 415 present in fluid 411 and inversely proportional to the volume of fluid 411. In some embodiments, changing the number of positive ions 415 in fluid 411 induces a change of volume in sealed chamber 403, to keep equilibrium with the osmolarity of fluid 410. In turn, the volume of sealed chamber 403 determines the amount of flow from channel 470 through channel 475 as membrane 401 opens or closes the aperture connecting channel 470 and channel 475. When the volume of the chamber 411 increases the membrane distends and occludes aperture 480, and narrows the fluidic path, reducing flow 405. Eventually the aperture connecting channel 470 with channel 475 may be blocked by membrane 401, stopping flow 405 completely. Thus, valve 400 can be set to variable flow positions by merely sending power to the electrodes. In addition, since the electrodes use only small amounts of power, the device may utilize low power to regulate the fluid flow through the valve. When osmolarity is equal in fluid 410 and in fluid 411, equilibrium is reached and the position of membrane 401 is steady. Once equilibrium is reached between the osmolarity of fluid 410 and the osmolarity of fluid 411, very small amounts of power may be used to maintain a specific set point. In some embodiments, once equilibrium is reached little to no power is used to maintain a set point. In some embodiments a set point for valve 401 may be fully open or fully closed, or may be an intermediate position such as illustrated in FIG. 4, as desired.

In some embodiments, the electrolytic solution included in fluid 411 may include copper sulfate, and the electrodes 421 and 422 may be formed of a conductive material such as platinum or gold. As such, positive ions 415 are copper ions. In such embodiments, applying a voltage through electrodes 421 and 422 results in electroplating some of the copper ions contained in the copper sulfate solution onto electrode 421 (negatively biased in this example) within sealed chamber 403. Electrode 422 (positively biased in this example) completes an electric circuit for electroplating. As copper ions in the electrolyte solution are plated onto electrode 421 they are consequently removed from solution and the number of total species contributing to the solution's osmotic pressure is reduced, reducing the osmolarity of fluid 411. In some embodiments, the electrolytic solution included in fluid 411 may be silver salts, such as silver halides. Some examples of silver salts used in an electrolyte solution in fluid 411 include, but are not limited to, silver bromide (AgBr), silver chloride (AgCl), silver iodide (AgI), and others, such as silver fluorides. In such embodiments, positive ions 415 include silver ions (Ag+, and Ag++). Other materials are also contemplated.

The use of copper and silver salts as electrolytes in fluid 411 is not limiting. One of ordinary skill would recognize that different electrolyte solutions may be used in fluid 411, consistent with embodiments disclosed herein. For example, some embodiments may use zinc sulfate, zinc chlorate, or nickel chloride solutions in fluid 411. The above salts and electrolytes are not limiting of embodiments consistent with the present disclosure, as other electrolyte solutions may be contemplated by one of ordinary skill.

As ions are removed from solution, osmolarity in fluid 411 eventually drops below that of fluid 410. Membrane 401 is permeable to water (or other solvent molecules), but not to positive ions 415 or negative ions or other species contributing to the osmotic pressure; therefore, net water diffusion through the membrane will be out of sealed chamber 403 and into the flow channel 470. In such configuration, the volume of the chamber defined in part by the membrane 401 decreases due to the outflow, increasing osmotic pressure inside sealed chamber 403, opening valve 400 to permit drainage fluid flow. The response time of valve 400 is limited by the diffusion rate of water or the solvent in fluid 411 through the membrane.

According to some embodiments, reducing the voltage between electrodes 421 and 422 to zero results in the gradual re-incorporation of positive ions 415 into solution in fluid 411. As the additional ion concentration increases the osmolarity in fluid 411, the resulting osmolarity imbalance will generate diffusion of water or solvent molecules from fluid 410 into sealed chamber 403. For example, when copper ions are positive ions 415, reducing the voltage difference between electrodes 421 and 422 allows copper ions to re-dissolve into the acidic Copper Sulfate electrolytic solution (which forms sulfuric acid as copper is removed from solution). This increases the volume of sealed chamber 403 until osmolarity in fluid 411 reaches equilibrium with osmolarity in fluid 410. The initial configuration is then recovered. The time it takes for valve 400 to recover the initial configuration may be determined by the speed of diffusion of the water or solvent molecules through membrane 401, and the time it takes for ions 415 to dissolve from the plating layer 425 into solution.

In some embodiments it may be desirable that the conducting material forming electrode 421 and electrode 422 have a higher electro-plating voltage than the material in plated layer 425. For example, when plated layer 425 is formed of copper, it is desirable to have electrodes 421 and 422 made of, for example, platinum or gold, which have a higher electro-plating voltage than copper. This ensures that when a positive voltage to electrode 421 is applied, ions from electrode 421 will not be transferred into fluid 411. Thus, in some embodiments it is desirable that the voltage difference applied between electrodes 421 and 422 has a value lower than an electro-plating voltage of the electrode material (e.g., copper or gold), and a higher voltage than an electro-plating voltage of a plating layer 425 formed of electrolyte ions (e.g., copper ions).

Because copper has a relatively low electro-plating potential, a low voltage may be used to remove plating layer 425 to increase the number of free ions in sealed chamber 403, and ultimately increase the volume of sealed chamber 403. The low voltage used ensures that material forming electrode 421 (such as platinum/gold) is not dissolved into fluid 411. Methods that prevent positive ions 415 from plating electrode 421 thus creating a valve 400 that can be actuated in either direction (inflate/deflate) rapidly are also contemplated. Such methods may include encapsulating electrode 421 with a material (e.g., polymer) that allows the flow of electrons, but not positive ions 415. In such embodiments, positive ions 415 may still form a densely packed layer 425 around a negatively biased electrode 421, without adhering to the electrode material.

Figure 5:
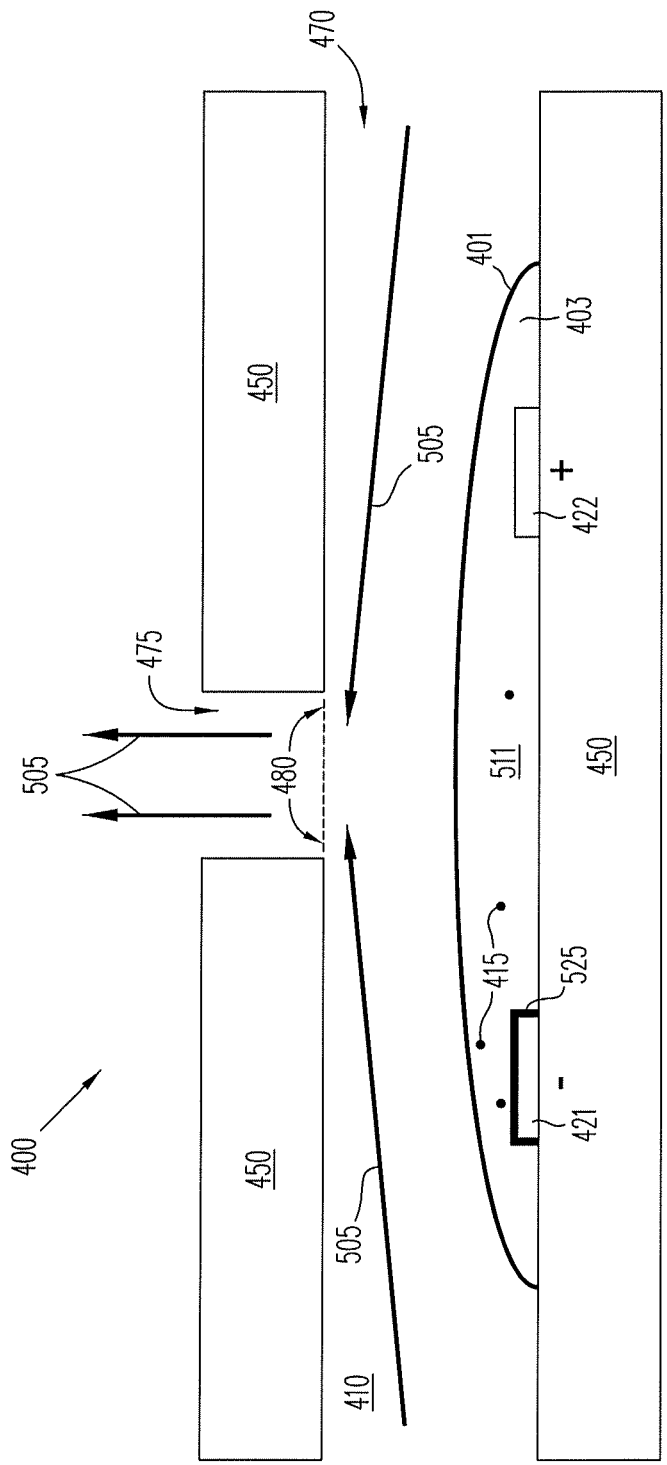
FIG. 5 shows a partial view of an osmotically actuated fluidic valve, according to some embodiments.

FIG. 5 shows a partial view of osmotically actuated fluidic valve 400, according to some embodiments. Valve 400 is in a fully open configuration in FIG. 5, showing almost complete depletion of ions 415 from solution in fluid 411. Fluid 511 includes the same components as fluid 411, but has a lower osmolarity due to the ions 415 that have been transferred to electrode 421. Ions 415 are mostly coalesced in a thick plating layer 525 on electrode 421 (negatively biased). The osmotic pressure has reached equilibrium by deflating membrane 401 to form a reduced volume in sealed chamber 403. Fluid may flow at a high flow rate from input channel 470 to output channel 475 as indicated by the arrows 505, since no constraint blocks the orifice in channel 475.

Figure 6:
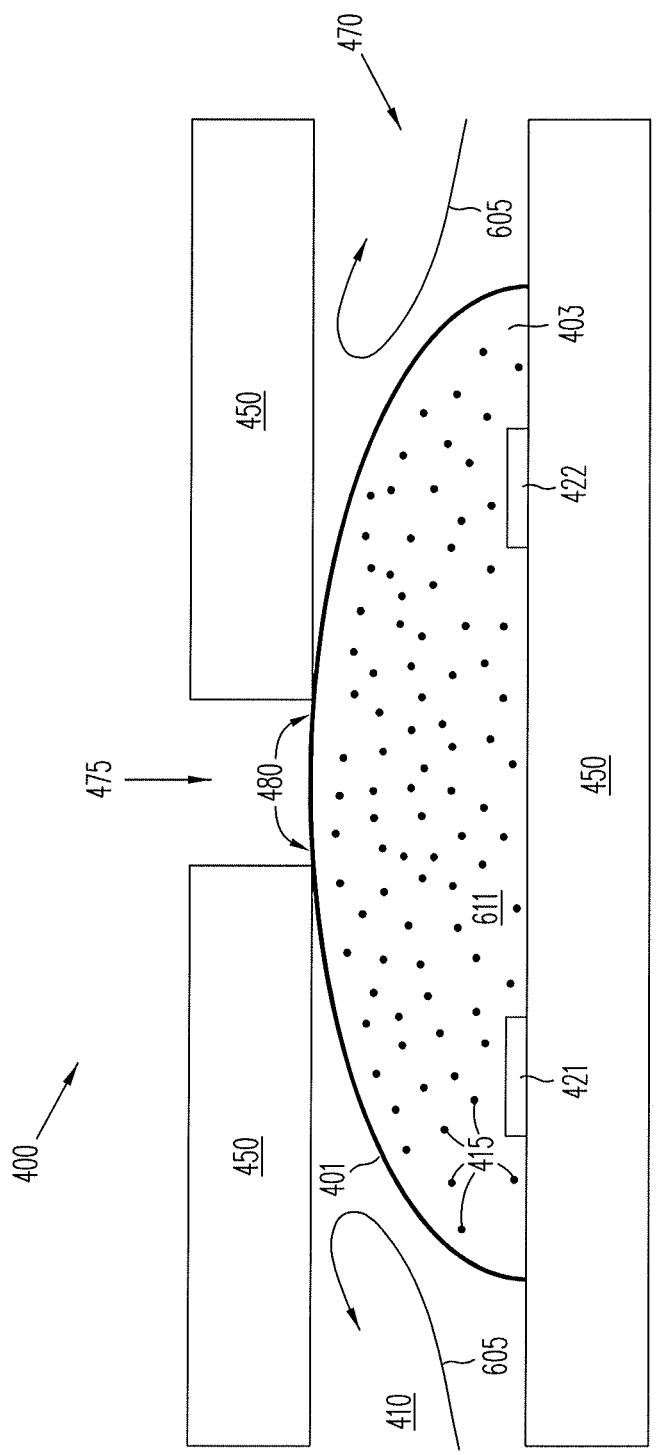
FIG. 6 shows a partial view of an osmotically actuated fluidic valve, according to some embodiments.

FIG. 6 shows a partial view of an osmotically actuated fluidic valve 400, according to some embodiments. Valve 400 is in a fully closed configuration in FIG. 6. In the configuration shown in FIG. 6 positive ions 415 are transferred from plating layer 425 into solution (cf. FIG. 4), in fluid 611. Fluid 611 includes the same components as fluid 411, but has a higher osmolarity due to the ions 415 that have been transferred from electrode 421. In some embodiments positive ions 415 may be copper ions, and the configuration in FIG. 6 may be obtained by letting the copper ions in plating layer 425 be re-dissolved into fluid 411. Thus, plating layer 425 is not shown in FIG. 6 because the ions forming the plate are dissolved into fluid 611. As copper ions re-enter solution, the osmolarity of fluid 411 raises above that of environment fluid 410, outside sealed chamber 403. Water or solvent molecules then flow through the semi-permeable membrane from fluid 410 to fluid 411 to equilibrate the osmolarity imbalance. Membrane 401 inflates due to the influx of water or solvent molecules into sealed chamber 403. In some embodiments, membrane 401 inflates to completely, or almost completely, block aperture 480, reducing flow 605. According to some embodiments, flow 605 may be completely stopped.

In some embodiments, osmotic pressure-based valve 400 may use little power for actuation. Furthermore, the valve opening may be set at any degree of variable opening between fully closed and fully opened. In some embodiments, flow control is established by adjusting the osmotic pressure within sealed chamber 403 applying a voltage difference between electrodes 421 and 422. According to some embodiments, once equilibrium between the osmolarity in fluid 410 and the osmolarity in fluid 411 is reached, a low amount of power is used to maintain a set point for valve 400. Furthermore, in some embodiments no power may be necessary to maintain the equilibrium configuration. Membrane 401, or a deformable diaphragm in membrane 401 may deform by several hundreds of microns. In some embodiments, membrane 401 or a deformable diaphragm in membrane 401, may deform by 1 mm, or up to 2 mm.

Similar osmotic pressure valve designs which utilize a semi-permeable membrane, and a mechanism other than electroplating to change the osmolarity of the solution, may be possible.

Figure 7:
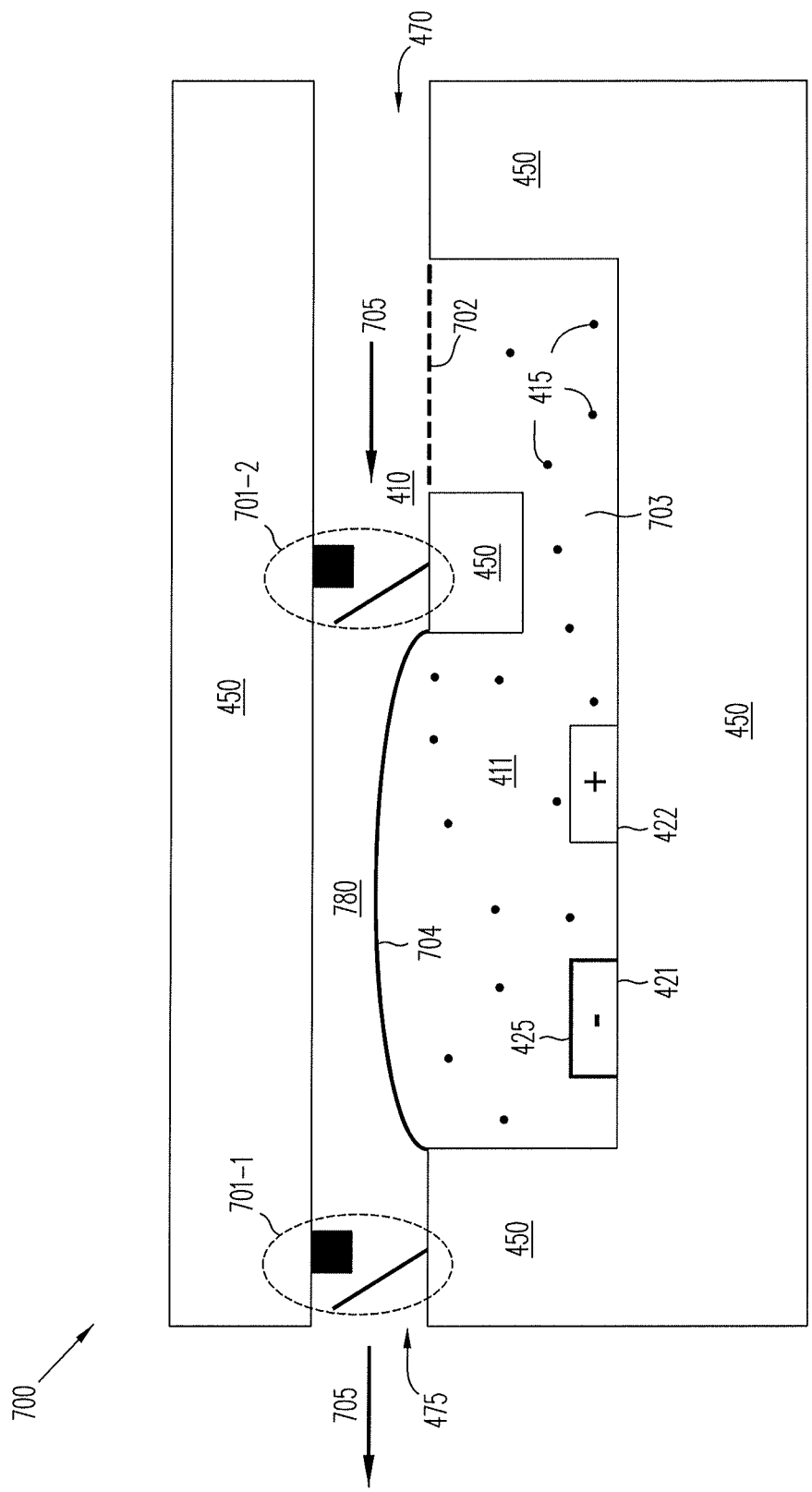
FIG. 7 shows a partial view of an osmotically actuated fluidic pump, according to some embodiments.

FIG. 7 shows a partial view of an osmotically actuated fluidic pump 700, according to some embodiments. The pump 700 may form a part of the IOP control system 200 described above, and may, for example, form a part of the valve system or other component of the system. Pump 700 allows fluid to flow as indicated by the arrows 705 from input fluidic channel 470 and output fluidic channel 475, through pump chamber 780. Input channel 470 and output channel 475 are formed in substrate 450, as described in detail above, in reference to FIG. 4. Pump 700 also includes sealed chamber 703 having fluid 411, as described in detail above in relation to FIG. 4. Sealed chamber 703 is separated from pump chamber 780 by a non-permeable, deformable membrane 704. In some embodiments, sealed chamber 703 is separated from input fluidic channel 470 by semi-permeable membrane 702.

In some embodiments, fluidic pump 700 includes the actuation of a diaphragm using osmotic pressure and semi-permeable, non-deformable membrane 702. In the example, shown in FIG. 7, fluidic pump 700 includes one or more check valves, such as one-way check valves 701-1, and 701-2 (collectively referred hereinafter as valves 701). Thus, as fluid flows from input fluidic channel 470 towards output fluidic channel 475, valves 701 are in an 'open' configuration. When fluid flows in the opposite direction, valves 701 are in a 'closed' configuration. Thus, valves 701 allow fluid flow 705 to flow in only one direction, as shown in FIG. 7.

The application and cessation of a voltage difference between electrodes 421 and 422 in a sequential manner may pump fluid from inlet channel 470 to output channel 475, as indicated by the arrows 705 in FIG. 7. By applying a voltage (negatively biased) to electrode 421 in relation to a voltage (positively biased) to electrode 422, the volume in chamber 703 containing fluid 411 decreases due to osmotically-driven flow through semi-permeable membrane 702, thereby increasing the volume of the pump chamber 780 as membrane 704 deflates. This induces fluid flow from the environment through input fluidic channel 470 into pump chamber 780, with valve 701-2 open while valve 701-1 is closed. Reducing the voltage bias between electrodes 421 and 422 to zero, ions 415 re-dissolve into fluid 411, increasing the volume of chamber 703 due to osmotically-driven flow through semi-permeable membrane 702. Thus, membrane 704 flexes, pushing fluid out of chamber 780, opening valve 701, and closing valve 701-2. The deflation-inflation cycle of membrane 704, combined with one-way check valves 701 results in a net transfer of fluid 410 from the environment, through channel 470 and channel 475 to a drainage location. The rate of transfer may be determined by the degree of deflation-inflation of membrane 704, and the frequency of operation of the cycle. The degree of deflation-inflation of membrane 704 is in turn controlled by the voltage difference applied between electrodes 421 and 422 and duration the voltage is applied.

In some embodiments, an osmotically actuated fluidic valve or pump, such as valve 400, or pump 700 may be used for applications such as drug delivery. For example, an environment fluid such as fluid 410 may include blood or a blood plasma. Further according to embodiments used for drug delivery, input fluidic channel 470 may be coupled to an environment including a solution having a drug dissolved in it. In such embodiments, output fluidic channel 475 may be coupled to an organ, a bodily cavity, or a blood vessel, for drug delivery.

Figure 8:
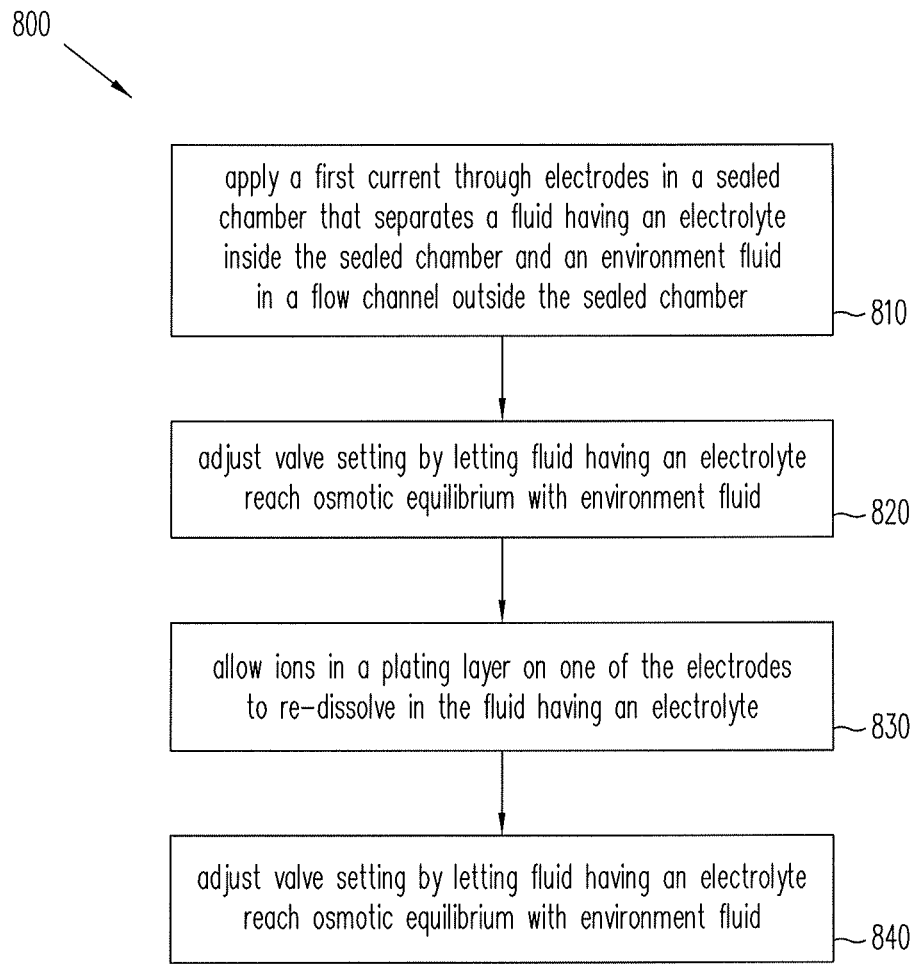
FIG. 8 shows a flow chart for a method to use an osmotically actuated fluidic valve, according to some embodiments.

FIG. 8 is a flow chart showing a method 800 of using an osmotically actuated fluidic valve, according to some embodiments. The osmotically actuated fluidic valve may be valve 400 described above (cf. FIG. 4). According to some embodiments, method 800 may be performed by a device such as ocular implant 350, described in detail above (cf. FIG. 3). For example, method 800 may be performed at least partially by processor 215 in combination with valve system 230 of the IOP control system 200, described in detail above (cf. FIG. 2). Method 800 may at least partially be stored as commands and instructions stored in memory 220 for the operation of processor 215.

Turning now to FIG. 8, at 810, a first current is applied through electrodes in a sealed chamber. The sealed chamber may be as chamber 403, and the electrodes may be as electrodes 421 and 422, described in detail above (cf. FIG. 4). Thus, the sealed chamber separates an environment fluid 410 in a flow channel 470 from a fluid 411 having an electrolyte, inside sealed chamber 403. In some embodiments, a semi-permeable membrane forms a wall in the sealed chamber to separate the environment fluid from the fluid having an electrolyte solution. In some embodiments, the wall separating the environment fluid from the fluid having the electrolyte solution includes a deformable diaphragm. In some embodiments, the semi-permeable membrane may be separated from the deformable diaphragm, and both separate the fluid including the electrolyte solution and the environmental fluid in the flow channel. The semi-permeable membrane may be as membrane 401 described in detail above (cf. FIG. 4).

In some embodiments, IOP control system 200 monitors pressure via sensor system 210 and applies current when processor 215 determines that the pressure should be adjusted to treat an ocular condition. For example, processor 215 may determine that IOP is higher than desired based on the feedback from sensor system 210. In response, processor 215 may apply a voltage to the electrodes in order to reduce the number of free ions in the chamber. This in turn results in an increased flow of fluid from inside the chamber, through the membrane, into the channel outside the chamber. Accordingly, the volume of the chamber decreases, correspondingly increasing the size of the channel at the aperture. This increase in size results in a higher flow and increased drainage through the valve, thereby lowering IOP from its undesirably elevated state.

In 810, the current may be applied for a short period of time. For example, in some embodiments, 810 includes applying a voltage between the electrodes in the sealed chamber. The voltage may be selected to produce a current so that a pre-selected amount of positive ions in the electrolyte solution forms a plating layer on the negatively biased electrode. Such plating layer may be as plating layer 425 on electrode 421 (cf. FIG. 4). The voltage applied in 810 may be lower than the electro-plating voltage of the material forming the electrodes. Thus, applying a voltage in 810 maintains the material integrity of the electrodes inside the sealed chamber, while inducing a plating of the positive electrolyte ions onto the plating layer. In some embodiments, the voltage applied in 810 may be about 2 Volts (V) or even less than 2 V. Other voltage levels are contemplated. Forming a plating layer on one of the electrodes, the osmolarity of the fluid in the sealed chamber may be reduced below the osmolarity of the environment fluid, such as fluid 410.

At 820, the valve setting is adjusted as a result of fluid in the sealed chamber reaching osmotic equilibrium with the environment fluid in the flow channel. According to some embodiments, 820 includes allowing solvent molecules to diffuse through the semi-permeable membrane from a location inside the sealed chamber to a location outside the sealed chamber. Furthermore, 820 may include allowing the semi-permeable membrane to deform as loss of solvent molecules decreases the fluid volume inside the sealed chamber. According to some embodiments, a wall separating the environment fluid from the fluid inside the sealed chamber may include a deformable and flexible diaphragm. In such embodiments, 820 may include allowing the diaphragm to deform accordingly. The result of 820 is a contraction of the deformable membrane, reducing the volume inside the sealed chamber. As a result, the flow path increases in size and the amount of environment fluid flow through valve 400 increases. Thus, the flow of an environment fluid may be regulated by following method 800. The valve adjustment at 820 may take any period of time. The time to adjust the valve setting may depend on the amount of current applied in 810 and on the volume change required in the sealed chamber 403 to reach equilibrium. The period of time may also depend on the thickness of semi-permeable membrane 401. Thus, the period of time may take a few seconds, up to several minutes, or even an hour or more, according to some embodiments. The period of time may be accelerated by applying small pulses of current to the electrodes. Furthermore, the train of current pulses applied to the electrodes may be selected in magnitude and time sequence in order to adjust the period of time to achieve a valve setting. For example, in some embodiments a train of pulses may be applied to maintain a selected osmolarity of the fluid in the sealed chamber, as ions in the plating layer may continuously re-dissolve into the fluid in the sealed chamber.

In 830, ions from the plating layer formed on an electrode are allowed to re-dissolve into the electrolyte solution in the fluid inside the sealed chamber. For example, 830 may include stopping the current flow through the electrodes by reducing the voltage bias between the electrodes to zero (0 V). 830 may take a few seconds, minutes, hours, or even more, according to some embodiments. A shorter or longer period of time in 830 may be selected based upon the desired fluid flow through the valve.

In 840, the valve setting is adjusted as the fluid in the sealed chamber is allowed to reach osmotic equilibrium with the environment fluid in the flow channel. 840 may include using the semi-permeable membrane in a similar manner to 820, but with solvent molecules moving from the flow channel outside the sealed chamber 403 to inside sealed chamber 403. Thus, in 840 the deformable membrane expands, resulting in a partial or total occlusion of an aperture fluidly connecting an input fluidic channel to an output fluidic channel in the valve. As a result, the flow paths decrease in size and the amount of environment fluid flow through valve 400 decreases.

In some embodiments, method 800 may be at least partially performed using an osmotically actuated fluidic pump, such as pump 700 described in detail above (cf. FIG. 7). 810 through 840 used with the osmotically actuated fluidic pump having one way valves result in the pumping of environment fluid from the environment to the drainage location coupled to the output fluidic channel.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An implantable fluidic valve actuated by osmotic pressure gradient including:
   an input fluid channel;
   an output fluid channel in fluid communication with the input fluid channel at an aperture;
   a semi-permeable membrane forming a portion of a sealed chamber, the semi-permeable membrane having an outer surface forming a wall of the input fluid channel, and having an inner surface forming a wall of the sealed chamber, the membrane being configured to allow diffusion of a solvent into and out of the sealed chamber; and
   a first electrode and a second electrode disposed within the sealed chamber configured to receive a voltage.

2. The implantable fluidic valve of claim 1 wherein the sealed chamber comprises an electrolyte solution.

3. The implantable fluidic valve of claim 2 wherein the electrolyte solution includes a compound selected from the group consisting of copper sulfate, zinc sulfate and a silver salt.

4. The implantable fluidic valve of claim 2 wherein the electrodes comprise a conducting material having an electro-plating voltage higher than an electro-plating voltage of a plated layer formed with ions from the electrolyte solution.

5. The implantable fluidic valve of claim 1 wherein the electrodes are made of a material selected from the group consisting of platinum and gold.

6. The implantable fluidic valve of claim 1 wherein the semi-permeable membrane comprises a non-porous material.

7. The implantable fluidic valve of claim 1 wherein the solvent is water.

8. The implantable fluidic valve of claim 1 further comprising an inlet tube in communication with the input fluid channel, the inlet tube being sized for implantation in an eye of a patient.

9. The implantable fluidic valve of claim 1 further comprising a one way check valve associated with one of the input and output fluid channels.

10. The implantable fluidic valve of claim 1, wherein the membrane is configured to displace from a first position relative to the aperture to a second position relative to the aperture to increase or decrease a fluid flow rate through the aperture.

11. The implantable fluidic valve of claim 1 further comprising a deformable and flexible diaphragm forming a part of the sealed chamber.

12. The implantable fluidic valve of claim 1, further comprising a processor and a sensor, the processor controlling voltage to the electrodes based on feedback from the sensor.

13. An ocular implant for treating an ocular condition, comprising:
   an inlet tube sized to receive aqueous humor; and
   an intra-ocular pressure (TOP) control system to regulate drainage of aqueous humor from the inlet tube; the TOP control system comprising a fluidic valve comprising:
      an input fluid channel coupled to the inlet tube;
      an output fluid channel in communication with the input fluid channel at an aperture; and
      a semi-permeable membrane configured to selectively displace relative to the aperture, the membrane having an outer side adjacent the input fluid channel and an inner side forming a part of a chamber, the chamber comprising:
         a first electrode and a second electrode configured to affect free ions in the chamber.

14. The ocular implant of claim 13 wherein the chamber comprises an electrolyte solution including copper sulfate.

15. The ocular implant of claim 13 wherein the first electrode and the second electrode comprise a conducting material having an electro-plating voltage higher than an electro-plating voltage of a plated layer formed with ions from an electrolyte solution disposed in the chamber.

16. An ocular implant for treating an ocular condition, comprising:
- an input fluid channel;
- an output fluid channel in fluid communication with the input fluid channel at an aperture;
- a semi-permeable membrane forming a portion of a sealed chamber, the semi-permeable membrane having an outer surface forming a wall of the input fluid channel, and having an inner surface forming a wall of the sealed chamber, the membrane being configured to allow diffusion of a solvent into and out of the sealed chamber; and
- a first electrode and a second electrode disposed within the sealed chamber to change a volume of the chamber.

17. The ocular implant of claim 16 further comprising a non-permeable membrane forming another portion of the sealed chamber, the non-permeable membrane having an inner surface forming another wall of the sealed chamber.

18. The ocular implant of claim 17 wherein the semi-permeable membrane is non-deformable and the non-permeable membrane is deformable.

19. The ocular implant of claim 17 further comprising:
- a first check valve positioned between the input fluid channel and the non-permeable membrane; and
- a second check valve positioned between the output fluid channel and the non-permeable membrane.

20. The ocular implant of claim 19 wherein the first check valve and second check valve are configured such that the first check valve closes and the second check valve opens when the non-permeable membrane deforms into a pump chamber defined between the first check valve and second check valve.

* * * * *